United States Patent [19]

Matta et al.

[11] Patent Number: 4,950,593
[45] Date of Patent: Aug. 21, 1990

[54] IMPROVED METHOD FOR ASSAYING PROTEOLYTIC ENZYMES

[75] Inventors: Michael S. Matta, Edwardsville; Raymond E. O'Bear, Granite City, both of Ill.

[73] Assignee: Vitek Systems, Inc., St. Louis, Mo.

[21] Appl. No.: 896,824

[22] Filed: Aug. 15, 1986

[51] Int. Cl.$^5$ ............................................. C12Q 1/38
[52] U.S. Cl. ...................................... 435/23; 435/24; 436/800; 548/161; 548/194
[58] Field of Search .................... 435/23, 24; 548/161, 548/194

[56] References Cited

U.S. PATENT DOCUMENTS

| | | | |
|---|---|---|---|
| 4,268,628 | 5/1981 | Klose et al. | 435/805 |
| 4,307,188 | 12/1981 | White | 436/527 |
| 4,405,711 | 9/1983 | Masuda et al. | 435/7 |

OTHER PUBLICATIONS

"Heterocyclic Azo Dyes by Oxidative Coupling", Hunig et al., Angen. Chem. Int'l. Edit. vol. 1, No. 12 (1962) pp. 640–646.

"Spot Test Detection and Colorimetric Determination of Aromatic Amines and Imino Heteroaromatic Compounds with 3-Methyl-2-benzothiazolone Hydrazone", Sawicki et al., Analytical Chemistry, vol. 33, No. 6, May 1961, pp. 722–725.

*Primary Examiner*—Sam Rosen
*Attorney, Agent, or Firm*—Veo Peoples, Jr.

[57] ABSTRACT

A reagent for proteolytic enzyme assays has the general formula

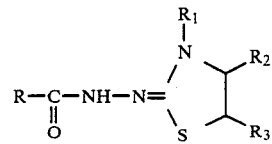

where RCO— is an enzyme reactive acyl, such as an amino acid, peptide or substituted amino acid or peptide. The reagent may be hydrolysed by proteolytic enzymes and developed to form a distinctive color. The reagent may be formed by reacting RCOOH with N-hydroxysuccinimide to form the acyl N-hydroxysuccinimide ester. The ester may then be reacted to form the reagent.

5 Claims, 1 Drawing Sheet

IMPROVED METHOD FOR ASSAYING PROTEOLYTIC ENZYMES

BACKGROUND AND SUMMARY OF THE INVENTION

Proteolytic assays play an important role in the diagnosis of pathological conditions, such as abnormalities in coagulation, in complement systems and in the identification of infectous agents. Common reagents for this purpose are paranitroanilide (PNA) derivatives of amino acids and peptides. PNA is commonly used to measure proteolytic activity. When contacted with enzymes present as a result of a particular pathological condition the PNA is released The presence of free PNA is measured colorimetrically. The released PNA is a yellow dye having an absorption maximum of 405 nanometers.

While PNA analysis if very useful, many body fluids, such as plasma, urine and spinal fluid absorb strongly at the wave length of PNA and thus give a very high background, which interfers with analysis of PNA tests. Applicants have discovered that it is advantageous to have an enzyme analysis system which works with a substrate having an absorption maximum at greater than about 500 nanometers, since this range (typically a blue/green color) provides high contrast and sensitivity and is not obscured by the background color of many body fluids. Applicants' have discovered and produced a series of such reagent materials which are effective in proteolytic enzyme assays and which can be read visually or electronically. Applicants' reagents can be used both in manual and in automatic analytical systems.

Applicants' have discovered that enzyme reactive acyl groups can be combined with a dye precursor, for example, a thizaolinone hydrazone (TH) or substituted thiazolinone hydrazone such as 3-methyl-2-benzothiazolinone hydrazone (MBTH) and the like, to produce a reagent which can be cleaved by proteolytic enzymes to free an indicator dye precursor, which can be developed. Applicants' reagent and system produce a highly sensitive, high contrast test.

It is thus an object of applicants' invention to produce a high contrast proteolytic enzyme test reagent.

It is a further object of applicants' invention to produce a test reagent which has an absorption maximum in the blue/green range.

It is an object of applicants' invention to produce a test reagent which utilizes an enzyme reactive acyl group combined with a dye moiety.

It is a further object of applicants' invention to provide a method of producing an enzyme assay substrate which will release a dye precursor.

It is a further object of applicants' invention to provide a method of testing proteolytic enzyme activity using a reagent substrate which will release a dye moiety on contact with a proteolytic enzyme.

DESCRIPTION OF THE DRAWING

The figure is a graph of the hydrolysis rate of one of applicants' substrates.

DESCRIPTION OF THE PREFERRED EMBODIMENTS

Figure 1:
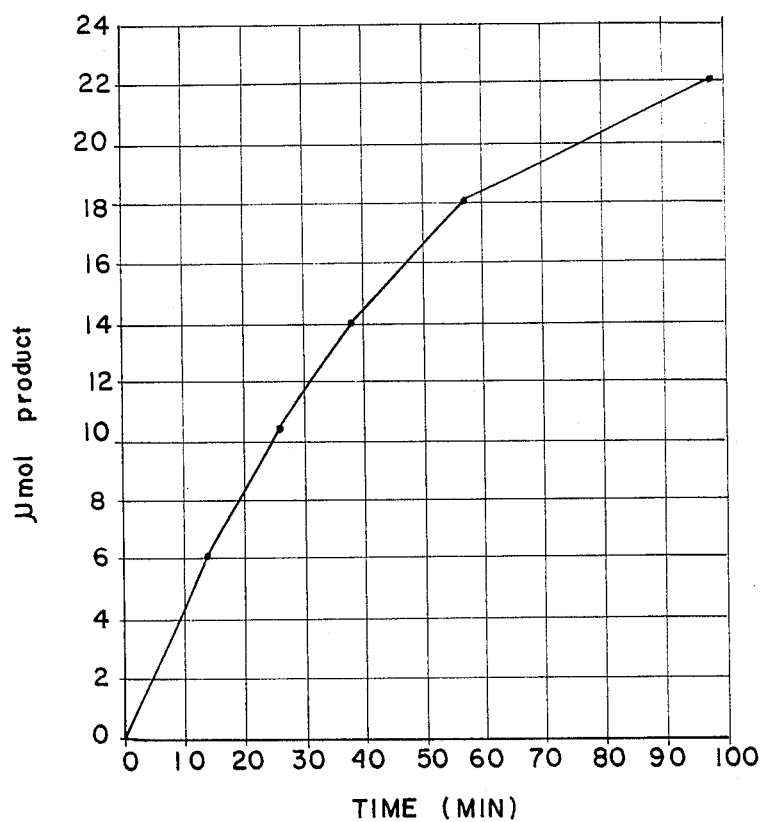

A new class of proteolytic enzyme substrates has been synthesized. These compounds are $^1$N-acyl derivatives of thiazolinone hydrazone or substituted thiazolinone hydrazone having the formula

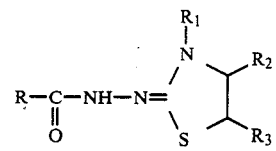

in which $R_1$, $R_2$ and $R_3$ may be H, aliphatic, cyclic, fused cylic, aromatic, fused aromatic, carboxylic, halogen, nitro, hydroxyl, amino, thio, esters and the like dye precusor substituents. For example, 3-methyl-2-benzothiazolinone hydrazone (MBTH) and substituted MBTH produce superior blue dyes. Preferably, RCO— is an amino acid, for example any of the 20 common amino acids, or an amino acid derivative, including peptides and their derivatives. The new substrates may be synthesized by the standard techniques of peptide synthesis. Applicants have found, however, that a particularly advantageous synthesis is one which reacts the acyl precursor with N-hydroxysuccinimide to produce an ester, followed by reacting the ester with the thilazolinone hydrazone.

The RCO-TH hydrolysis is catalyzed by proteolytic enzymes to give a carboxylic acid RCOOH and TH. The hydrolysis product TH may be detected spectrophotometrically by oxidative coupling with aromatic amines or phenols, for example 3-dimethylaminobenzoic acid (DMAB) or equivalent oxidative coupling agents. The reaction mixtures for detection of the color preferably include an oxidizing agent, for example, ferricyanide or the peroxidase-hydrogen peroxide system, for color development. The dye produced in the system with MBTH and DMAB maximally absorbs at 590 nm and is intensely colored, with molar absorptivity of 57,000 $M^{-1}cm^{-1}$ at the typical assay conditions.

The invention may be more thoroughly understood by reference to the included examples which describe the synthesis of amides of the type RCO-MBTH (Examples 1–15) and a continuous enzyme assay (Example 16). A discontinuous assay is illustrated in Example 17. Example 18 is a determination of the kinetic catalytic constant ($k_c$) and binding constant ($K_m$) for trypsin-catalyzed hydrolysis of an RCO-MBTH substrate by the continuous assay method.

Suitable criteria for identification and purity of applicants' substrates per the above examples generally include: (1) production of at least 90% of the theoretically calculated amount of blue color at 590 nm in the standard color test upon cleavage by trypsin; (2) product homogeneity or near homogeneity as indicated by partition thin-layer chromatography on silica gel in a solvent system of sec-butyl alcohol/3% aqueous ammonia (100:44 V/V) with spot detection by iodine vapor and long-wavelength ultraviolet light; (3) agreement between the theoretically expected and experimentally obtained proton-decoupled C-13 nuclear magnetic resonance spectra in 99.9 atom %D dimethylsulfoxide-$d_6$ 15.0 at MHz. (4) amino acid analysis of hydrolysates of RCO-TH. The first test, color development of tryptic digests, is limited to compounds containing an Arg-MBTH or Lys-MBTH linkage. These amino acid residues are required to obtain sufficient tryptic reactivity to carry the reaction to completion with a reasonable time for the test. Other amino acid-MBTH linkages may be split more rapidly by other enzymes, but the above criteria are suitable as a standard.

EXAMPLE 1

¹N-(N-t-butoxycarbonyl)-L-phenylalanyl 3-methyl-2-benzothiazolinone hydrazone)

In a 125-ml erlenmeyer flask, 35 mmol (12.7 g) of the N-hydroxysuccinimide ester of Boc-L-phenylalanin ® was added to 70 mL of acetonitrile (HPLC grade) followed by the addition of 33.4 mmol (6.0 g) of 3-methyl-2-benzothiazolinone hydrazone (MBTH). The reaction mixture was stirred at room temperature for 24 h. The colorless precipitate was collected by filtration washed with 10 mL cold acetonitrile and dried at reduced pressure Boc-L-PHE-MBTH: Yield 11.8 g (83%), m.p. 182° C.

EXAMPLE 2

¹N-(N-benzyloxycarbonyl)-L-phenylalanyl 3-methyl-2-benzothiazolinone hydrazone)

In a 125-mL erlenmeyer flask, 35 mmol (13.9 g) of the N-hydroxysuccinimide ester of Z-L-phenylalanine was added to 70 mL of acetonitrile (HPLC grade) followed by the addition of 33.4 mmol (6.0 g) of 3-methyl-2-benzothiazolinone hydrazone. The reaction mixture was stirred at room temperature for 24 h. The colorless precipitate was collected by filtration, washed with 10 mL cold acetonitrile and dried at reduced pressure.

Z-L-PHE-MBTH: Yield 12.3 g (80%), m.p. 178° C.

EXAMPLE 3

¹N-(N-benzyloxycarbonyl)-D-phenylalanyl 3-methyl-2-benzothiazolinone hydrazone)

In a 125-mL erlenmeyer flask, 35 mmol (13.9 g) of the N-hydroxysuccinimide ester of Z-D-phenylalanine was added to 70mL of acetonitrile (HPLC grade) followed by the addition of 33.4 mmol (6.0 g) of 3-methyl-2-benzothiazolinone hydrazone. The reaction mixture was stirred at room temperature for 24 h. The colorless precipitate was collected by filtration, washed with 10 mL cold acetonitrile and dried at reduced pressure.

Z-D-PHE-MBTH: Yield 11.4 g (74%), m.p. 176° C.

EXAMPLE 4

¹N-(N-t-butoxycarbonyl)-L-alanyl 3-methyl-2-benzo thiazolinone hydrazone)

In a 125-mL erlenmeyer flask, 35 mmol (10.0 g) of the N-hydroxysuccinimide ester of Boc-L-alanine was added to 70 mL of acetonitrile (HPLC grade) followed by the addition of 33.4 mmol (6.0 g) of 3-methyl-2-benzothiazolinone hydrazone. The reaction mixture was stirred at room temperature for 24 h. The colorless precipitate was collected by filtration, washed with 10 mL cold acetonitrile and dried at reduced pressure.

Boc-L-ALA-MBTH: Yield 7.8 g (67%), m.p. 181° C.

EXAMPLE 5

¹N-(N-t-butoxycarbonyl)-S-benzyl-L-cysteinyl 3-methyl2-benzothiazolinone hydrazone)

In a 125 mL erlenmeyer flask, 35 mmol (14.3 g) of the N-hydroxysuccinimide ester of Boc-L-(Bz)cysteine was added to 70 mL of acetonitrile (HPLC grade) followed by the addition of 33.4 mmol (6.0 g) of 3-methyl-2-benzothiazolinone hydrazone. The reaction mixture was stirred at room temperature for 24 h. The colorless precipitate was collected by filtration, washed with 10 mL cold acetonitrile and dried at reduced pressure.

Boc-L-(Bz)CYS-MBTH: Yield 11.3 g (72%), m.p., 144°–146° C.

EXAMPLE 6

¹N-(N-t-butoxycarbonyl)-L-methionyl 3-methyl-2-benzothiazolinone hydrazone)

In a 125-mL erlenmeyer flask, 35 mmol (12.1 g) of the N-hydroxysuccinimide ester of Boc-L-methionine was added to 70 mL of acetonitrile (HPLC grade) followed by the addition of 33.4 mmol (6.0 g) of 3-methyl-2-benzothiazolinone hydrazone. The reaction mixture was stirred at room temperature for 24 h. The colorless precipitate was collected by filtration, washed with 10 mL cold acetonitrile and dried at reduced pressure.

Boc-L-MET-MBTH: Yield 10.7 g (78%), m.p. 157° C.

EXAMPLE 7

¹N-(N-benzyloxycarbonyl)-L-prolyl 3-methyl-2-benzothiazolinone hydrazone)

In a 125-mL erlenmeyer flask, 35 mmol (12.1 g) of the N-hydroxysuccinimide ester of Z-L-proline was added to 70 mL of acetonitrile (HPLC grade) followed by the addition of 33.4 mmol (6.0 g) of 3-methyl-2-benzothiazolinone hydrazone. The reaction mixture was stirred at room temperature for 24 h. The colorless precipitate was collected by filtration, washed with 10 mL of cold acetonitrile and dried at reduced pressure.

Z-L-PRO-MBTH: Yield 7.1 g (52%), m.p. 188° C.

EXAMPLE 8

¹N-(N-t-butoxycarbonyl-γbenzyl-L-glutamyl 3-methyl-2-benzothiazolinone hydrazone)

In a 125-mL erlenmeyer flask, 35 mmol (15.3 g) of the N-hydroxysuccinimide ester of Boc-L-(Bz)glutamic acid was added 70 mL of acetonitrile (HPLC grade) followed by the addition of 33.4 mmol (6.0 g) of 3-methyl-2-benzothiazolinone hydrazone. The reaction mixture was stirred at room temperature for 24 h. The colorless precipitate was collected filtration, washed with 10 mL cold acetonitrile and dried at reduced pressure.

Boc-L-(Bz)GLU-MBTH: Yield 12.3 g (74%), m.p. 131°–133° C.

EXAMPLE 9

¹N-(N-t-butoxycarbonyl)glycyl 3-methyl-2-benzothiazolinone hydrazone)

In a 125-mL erlenmeyer flask, 35 mmol (9.5 g of the N-hydroxysuccinimide ester of Boc-glycine was added to 70 mL of acetonitrile (HPLC grade) followed by the addition of 33.4 mmol (6.0 g) of 3-methyl-2-benzothiazolinone hydrazone. The reaction mixture was stirred at room temperature for 24 h. The colorless precipitate was collected by filtration, washed with 10 mL cold acetonitrile, and dried at reduced pressure.

Boc-GLY-MBTH: Yield 5.75 g (51%), m.p. 169°–170° C.

EXAMPLE 10

¹N-(N-t-butoxycarbonyl)-L-leucyl 3-methyl-2-benzothiazolinone hydrazone)

In a 125-mL erlenmeyer flask, 35 mmol (11.5 g) of the N-hydroxysuccinimide ester of Boc-L-leucine was added tc 70 mL of acetonitrile (HPLC grade) followed by the addition of 33.4 mmol (6.0 g) of 3-methyl-2-benzothiazolinone hydrazone. The reaction mixture was stirred at room temperature for 24 h. The colorless precipitate was collected by filtration, washed with 10 mL cold acetonitrile and dried at reduced pressure.

Boc-L-LEU-MBTH: Yield 8.5 g (70%), m.p. 120° C.

EXAMPLE 11

1N-(N-t-butoxycarbonyl)-0-benzyl-L-threonyl 3-methyl-2- benzothiazolinone hydrazone)

In a 125-mL erlenmeyer flask, 35 mmol (14.2 g) of the N-hydroxysuccinimide ester of Boc-L-(Bz)threonine was added to 70 mL of acetonitrile (HPLC grade) followed by the addition of 33.4 mmol (6.0 g) of 3-methyl-2-benzothiazolinone hydrazone. The reaction mixture was stirred at room temperature for 24 h. The colorless precipitate was collected by filtration, washed with 10 mL cold acetonitrile and dried at reduced pressure.

Boc-L-(Bz)THR-MBTH: Yield 13.5 g (86%), m.p. 122°–126° C.

EXAMPLE 12

1N-(Di-N-benzyloxycarbonyl)-L-lYsyl 3-methyl-2-benzothiazolinone hydrazone)

In a 125-mL erlenmeyer flask, 35 mmol (17.9 g) of the N hydroxysuccinimide ester of Di-Z-L-lysine was added to 70 mL of acetonitrile (HPLC grade) followed by the addition of 33.4 mmol (6.0 g) of 3-mthyl-2-benzothiazolinone hydrazone. The reaction mixture was stirred at room temperature for 24 h. The colorless precipitate was collected by filtration, washed with 10 mL cold acetonitrile and dried at reduced pressure.

Di-Z-L-LYS-MBTH: Yield 17.0 g (88%), m.p. 169°–170° C.

EXAMPLE 13

1N-(N-α-t-butoxycarbonyl)argininyl 3-methyl-2-benzothiazolinone hydrazone)

A solution of 6.68 g (21.5 mmol) of (N-α-t-butoxycarbonyl)arginine hydrochloride and 2.17 g (21.5 mmol) of N-methylmorpholine in 50 mL of dry N,N-dimethylformamide (DMF) in a 100-mL round-bottomed flask was cooled to −10° C. in an ice-salt bath. To the stirred, cooled solution was added dropwise with stirring 2.93 g (21.5 mmol) of isobutyl chloroformate. The reaction mixture was maintained at −10° C. for 15 minutes, then 3.85 g (21.5 mmol) of 3-methyl-2-benzothiazolinone (MBTH) was added in one batch. Gas evolution and a change from colorless to amber was observed within 1–5 minutes of the addition of the MBTH, after which the reaction mixture was permitted to come to room temperature for 24 h. The precipitated N-methylmorpholine hydrochloride was removed by filtration and the clear amber supernatent was added to 500 ml, of deionized water. The aqueous solution was brought to pH 8 by addition of solid sodium bicarbonate. Occasionally a color change from amber to green was observed upon adjustment of the pH. The solution was transferred to a 2L separatory funnel, shaken vigorously with 800 mL of methylene chloride, and the yellow methylene chloride layer was removed. Upon standing at room temperature for 5 minutes to 8 h, a solid product precipitated from the colorless aqueous layer. The product was removed by filtration and dried at reduced pressure to give a colorless or pale yellow powder as the bicarbonate salt of the product.

EXAMPLE 14

1N-(N-benzoyl-L-phenylalanyl-L-valyl)-L-arginyl 3-methyl- 2-benzothiazolinone hydrazone)

In a 125-mL erlenmeyer flask, 1.6 mmol (0.90 g) of the N-hydroxysuccinimide ester of N-benzoyl-L-phenylalanyl-L-valine was dissolved in 20 mL acetonitrile (HPLC grade). A solution containing 4.8 mmol (0.40 g) of sodium bicarbonate in 40 mL of water was added, with stirring, followed by 1.6 mmol (0.72 g) of 1N-arginyl 3-methyl-2-benzothiazolinone hydrazone-3HCl. After 24 h at room temperature, the colorless precipitate was collected by filtration and washed with 10 mL of cold water and dried at reduced pressure. The bicarbonate salt of the product was produced in 71% yield (0.82 g).

EXAMPLE 15

1N-(N-t-butoxycarbonyl-L-leucylglycyl)-L-arginyl 3-methyl-2-benzothiazolinone hydrazone)

In a 50-mL erlenmeyer flask, 3.9 mmol (1.5 g) of the N-hydroxysuccinimide ester of N-t-butoxycarbonyl-L-leucyl glycine dissolved in 20 mL of dry dimethylformamide (HPLC grade). With stirring, 13 mL of a 5% (w/v) solution of sodium bicarbonate was added, followed by a 3.9 mmol (1.75 g) of the trihydrochloride salt of 1N-arginyl 3-methyl-benzothiazolinone hydrazone. After 24 h at room temperature the residual sodium bicarbonate was removed by filtration. Evaporation of the filtrate at reduced pressure produced the bicarbonate salt of the title compound as a pale yellow solid. The product was washed twice with 10 mL of cold water and dried at reduced pressure; 67% yield (1.76 g).

EXAMPLE 16

Saturation kinetics for N-(N-benzyloxycarbonyl)glycyl-L-prolyl-L-arginyl 3-methyl-2-benzothiazolinone hydrazone with trypsin) .

A continuous assay for trypsin was performed, i.e., the oxidizing and coupling reagents for color development were included with the substrate in the reaction mixture so that color development may be monitored on a continuous basis with time. In this example the dye precursor is developed to a dye without destroying the enzymatic activity of the enzyme. The reaction was initiated by the addition of 0.1 mL of enzyme (10 μg/mL) to 0.9 mL of buffer solution containing substrate (Z-GLY-PRO-ARG-MBTH) and color developing reagents. The final concentrations in the cuvette were 1 μg trypsin +0.14 M Tris buffer, pH 7.8 +0.0131 M 3-dimethylamino benzoic acid (DMAB) +0.002 M potassium ferricyanide +3% dimethylformamide +substrate. Substrate concentrations of $1.74 \times 10^{-3}$M, $5.8 \times 10^{-4}$M and $3.9 \times 10^{-4}$M were assayed in triplicate. The increases in absorbance at 590 nm were monitored continuously for 5 minutes and the initial rates determined. Using the molar absorptivity of 57,000 for the chromogen produced (MBTH-DMAB), the average rate of hydrolysis was calculated to be $4.43 \pm 0.1 \times 10^{-6}$ mol min$^{-1}$.

EXAMPLE 17

Discontinuous, peroxidase-coupled assay of α-chymotrypsin Using N-(N-benzyloxycarbonyl)-L-phenylalanyl 3-methyl-2-benzothiazolinone hydrazone (Z-L-PHE-MBTH).

In this example the enzyme is permitted to hydrolyse the substrate in the absence of oxidizer and coupling agent. Color development is initiated by addition of oxidizer and coupling agent and the color absorption is measured on a spectrophotometer. An amount of substrate needed to give a 3.2 mM solution was dissolved in 10 mL dimethylformamide. To 30 mL of 0.1 M phosphate buffer, pH 8.0, 1.0 mL of the stock substrate solution was added. The reaction was initiated by the addition of 1.0 mL of α-chymotrypsin stock solution (50 mg/mL in 0.1 M acetate buffer, pH 5.0). At t=0 and periodically over a 90 minute time span, 1.0 mL aliquots were removed and added to a 3.0 mL color developing solution containing 0.0083 M 3-dimethylamino benzoic acid (DMAB) +0.1% hydrogen peroxide +10 μg horseradish peroxidase. After 2 minutes, the absorbence at 590 nm was recorded. At the conditions used the chromogen (DMAB-MBTH) had a molar absorptivity of 65,000. FIG. 1 shows the rate of hydrolysis of Z-L-PHE-MBTH, as indicated by the appearance of MBTH.

EXAMPLE 18

Determination of the Kinetic Constants for the Trypsin Catalyzed Hydrolysis of N-(N-t-butoxycarbonyl)-L-Arginyl 3-methyl benzothiazolinone hydrazone (continuous assay)).

In a one cm. cuvette were mixed 3.0 mL of 0.02 M tris buffer, pH 7.8, containing 0.02 M 3-dimethylamino benzoic acid (DMAB) 0.1 mL of 0.065 M potassium ferricyanide, and 0.1 mL of substrate (Boc-ARG-MBTH). The reaction was initiated by the addition of 1 0.1 mL of trypsin ($2.33 \times 10^{-4}$ M in 0.1 M pyrophosphate buffer, pH 8.3). Eight concentrations of substrate, from $9.98 \times 10^{-4}$ M to $7.8 \times 10^{-6}$ M, were assayed in triplicate. The increase in absorption at 590 nm was monitored continuously and the initial rates were determined. Under the conditions of the assay, a molar absorptivity of 57,000 was used to determine the concentration of the chromogen (MBTH-DMAB) produced by the hydrolysis of substrate. Table I contains the date used to determine the binding and kinetic constants ($K_m$, $k_c$). A Lineweaver-Burk plot yielded respective values of $K_m$ and $k_c$ of $1.41 \times 10^{-3}$ M and $4.36 \times 10^{-2} s^{-1}$. analysis by the Woolf-Augustinssen-Hofstee method gave $K_m = 1.29 \times 10^{-3}$ M and $k_c = 4.28 \times 10^{-2} s^{-1}$.

TABLE I

| 1/V (min M$^{-1}$) | 1/S (M$^{-1}$) | V/S (min$^{-1}$) |
| --- | --- | --- |
| 0.000565 |  | 0.00177 |
| 0.000528 | 100 | 0.00190 |
| 0.000625 |  | 0.00160 |
| 0.000699 |  | 0.00287 |
| 0.000742 | 200 | 0.00270 |
| 0.000742 |  | 0.00270 |
| 0.000766 |  | 0.00523 |
| 0.000880 | 401 | 0.00456 |
| 0.000819 |  | 0.00489 |
| 0.001033 |  | 0.00776 |
| 0.001080 | 802 | 0.00743 |
| 0.001188 |  | 0.00675 |
| 0.001697 |  | 0.00945 |
| 0.001697 | 1603 | 0.00945 |
| 0.001827 |  | 0.00877 |
| 0.002969 |  | 0.01808 |
| 0.002969 | 2305 | 0.01080 |
| 0.003393 |  | 0.00945 |
| 0.005056 |  | 0.01268 |
| 0.005056 | 6413 | 0.01268 |
| 0.005280 |  | 0.01215 |
| 0.009901 |  | 0.01295 |
| 0.009901 | 12826 | 0.01295 |
| 0.009506 |  | 0.01349 |

We claim:

1. A method for detecting the presence of proteolytic enzymes in an assay sample comprising:
   a. contacting an assay sample with a thiazolinone hydrazone compound having the formula:

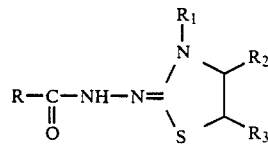

wherein RCO - is an enzyme reactive acyl constituent which, in the presence of proteolytic enzyme, will release from the hydrazone substituent, sid acyl being selected from the group consisting of amino acids, peptides, and substituted peptides; and wherein $R_1$ is selected from the group consisting of hydrogen, aliphatic, cyclic, aromatic, carboxylic, halogen, hydroxyl, amino, and thio substituents; and wherein $R_2$ and $R_3$ are selected from the group consisting of aliphatic, cyclic, aromatic, cart,oxylic, halogen, nitro, hydroxyl, amino, thio, fused cyclic, and fused aromatic;
   b. adding oxidative coupling agents and oxidizing agents for the thiazolinone to develop blue-green chromogens; and
   c. monitoring the increase in absorbance at 590 nanometers;
   whereby the color develops while retaining the enzymatic activity of the proteolytic enzyme and the concentration of the chromogens is directly proportional to the degree of enzymatic activity.

2. The method of claim 1 wherein the assay method is conducted continuously by having the oxidative coupling agents and the oxidizing agent present in the assay with the compound of Step (a) and monitoring the absorbance continuously with time.

3. The method of claim 1 wherein the assay method is conducted discontinuously by periodically removing aliquots of the assay at Step (a), adding the oxidizing agents and oxidative coupling agents of Step (b) to each aliquot and recording its absorbance at that period of time.

4. The method of claim 1 wherein the constituent attached to the enzyme reactive acyl is MBTH.

5. The method of claim 1 wherein $R_2$ and $R_3$ are joined in either a fused cyclic or fused aromatic ring.

* * * * *